United States Patent [19]

Duby et al.

[11] Patent Number: 5,280,127
[45] Date of Patent: Jan. 18, 1994

[54] PYRROLINE-BASED FOOD FLAVORING COMPOUNDS

[75] Inventors: Philippe Duby, Prilly; Tuong Huynh-Ba, Pully, both of Switzerland

[73] Assignee: Nestec S.A., Vevey, Switzerland

[21] Appl. No.: 979,293

[22] Filed: Nov. 20, 1992

[30] Foreign Application Priority Data

Dec. 2, 1991 [CH] Switzerland ............... 3529/91

[51] Int. Cl.⁵ .............................. C07D 207/20
[52] U.S. Cl. .................................... 548/565
[58] Field of Search ........................ 548/565

[56] References Cited

U.S. PATENT DOCUMENTS 3,620,771 11/1971 Hunter .
3,725,425 4/1973 Hunter .
4,522,838 6/1985 Buttery et al. ............... 426/537

FOREIGN PATENT DOCUMENTS 0436481 7/1991 European Pat. Off. .
0125364 10/1981 Japan ............................. 548/565
1167809 10/1969 United Kingdom ........... 548/565

OTHER PUBLICATIONS

Buchi, et al., Synthesis of 2-acetyl-1,4,5,6-tetra-hydropyridine, a constituent of bread aroma, The Journal of Organic Chemistry, vol. 36, No. 1, Jan. 1971; pp. 609–610.

Primary Examiner—Mary C. Lee
Assistant Examiner—Jacqueline Haley
Attorney, Agent, or Firm—Vogt & O'Donnell

[57] ABSTRACT

2-(1-alkoxyethenyl)-1-pyrroline compounds. The compounds may be employed for preparing food flavorant compositions, and 2-(1-ethoxyethenyl)-1-pyrroline, in particular, has characteristics suiting it as a flavoring agent for food products.

2 Claims, No Drawings

PYRROLINE-BASED FOOD FLAVORING COMPOUNDS

BACKGROUND OF THE INVENTION

The present invention relates to pyrroline-based compounds, their production, and uses thereof.

This invention relates to a process for the production of 2-acetyl-1-pyrroline in encapsulated form, to the encapsulated product obtained and to a particular use thereof. The present invention also relates to a new compound of the pyrroline family from which encapsulated 2-acetyl-1-pyrroline can be obtained, to a process for its production and to a particular use.

U.S. Pat. No. 4,522,838 (Buttery, et al.), describes a process for the production of 2-acetyl-1-pyrroline. This process comprises catalytically reducing 2-acetyl pyrrole for 15 hours under a hydrogen pressure of approximately 0.7 bar, to obtain (1-hydroxyethyl)-2-pyrrolidine as an intermediate product, and oxidizing the intermediate product obtained with silver carbonate under reflux in benzene, again over a period of 15 hours. The 2-acetyl-1-pyrroline is then isolated by gas phase chromatography using a capillary column 2 meters in length and 6.4 mm in diameter. The 2-acetyl-1-pyrroline thus obtained has a purity of approximately 95%, but can only be produced in small quantities at a time, due mainly to the purification of the compound by gas phase chromatography. In addition, the 2-acetyl-1-pyrroline is unstable and has to be stored at a temperature preferably below 0° C., which makes it difficult to use, particularly on an industrial scale.

Another process for the production of 2-acetyl-1-pyrroline from pyrrolidine is known from European Patent Application Publication No. 436 481, but does not solve the problem in question.

SUMMARY OF THE INVENTION

The present invention provides 2-(1-alkoxyethenyl)-1-pyrroline compounds, including 2-(1-ethoxyethenyl)-1-pyrroline.

The alkoxyethenyl compounds provide for production of 2-acetyl-1-pyrroline in a stable form which can be stored for a certain time at ambient temperature. In addition, the ethoxyethenyl compound, in particular, may be employed as a flavoring agent for a food product by itself or as part of a composition containing the same suitable for addition to a food product. The present invention also, therefore, provides a composition containing 2-(1-ethoxyethenyl)-1-pyrroline which is suitable for addition to a food product for flavoring a food product. Hence, the present invention also includes a process for using the ethoxyethenyl compound, or a composition containing the same, wherein such is added to a food product, and therefore also includes a food product having the ethoxyethenyl compound or a composition containing the same added thereto.

DETAILED DESCRIPTION OF THE INVENTION

The present invention provides a process in which a 2-(1-alkoxyethenyl)-1-pyrroline is hydrolyzed with an acid, the reaction mixture is neutralized with an equimolar quantity of base, a solution of cyclodextrin is added to give a solution containing up to 20% by weight 2-acetyl-1-pyrroline, based on the cyclodextrin, and the solution is freeze-dried to obtain a powder which may contain up to 20% by weight 2-acetyl-1-pyrroline.

The present invention also provides a process in which 2-(1-alkoxyethenyl)-1-pyrroline is hydrolyzed with an acid, the reaction mixture is neutralized with an equimolar quantity of base, a solution of maltodextrin is added to obtain a solution containing up to 10% by weight 2-acetyl-1-pyrroline, based on the maltodextrin, and the solution is freeze-dried to obtain a powder which may contain up to 10% by weight 2-acetyl-1-pyrroline.

A product in the form of a powder which may contain up to 20% by weight encapsulated 2-acetyl-1-pyrroline can be obtained by this process. Stable 2-acetyl-1-pyrroline can thus be produced in large quantities on an industrial scale, being far easier to store and/or use than substantially pure 2-acetyl-1-pyrroline.

In the first process noted above, a 2-(1-alkoxyethenyl)-1-pyrroline, preferably in the form of a 2 to 30% solution, is hydrolyzed with an acid, preferably a mineral acid, such as hydrochloric acid. The mixture obtained may then be diluted and the acid added is neutralized by addition of an equimolar quantity of base, preferably a strong base, such as sodium hydroxide. A solution of cyclodextrin or maltodextrin is then added to the neutralized mixture. A solution of β-cyclodextrin is preferably added. A solution containing one or more cyclodextrins and maltodextrin may also be added.

Cyclodextrin is added in such a quantity that a solution containing up to 20% 2-acetyl-1-pyrroline, based on the cyclodextrin, is obtained. If maltodextrin is used, it is added in such a quantity that a solution containing up to 10% 2-acetyl-1-pyrroline, based on the maltodextrin, is obtained.

The various steps involved in this process are preferably carried out at a temperature ranging from −10° C. to 25° C., although it is important to bear in mind the fact that the higher the temperature, the greater the risk of decomposition of the 2-acetyl-1-pyrroline and the greater the need to work quickly if this risk is to be reduced.

The solution thus obtained is then freeze-dried and gives an encapsulated product in the form of a powder which may contain up to 20% by weight 2-acetyl-1-pyrroline. It has also surprisingly been found that the encapsulated product thus obtained can be used to strengthen the taste of certain food products, and as shown in the Examples, the encapsulated product may be used either on its own or in combination with other compounds for flavoring food products.

As will be appreciated, the 2-(1-alkoxyethenyl)-1-pyrroline compounds employed as a starting material in the two processes described above correspond to the following general formula:

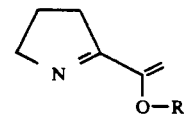

with R=alkyl.

These compounds may be obtained by a process in which the corresponding alkyl vinylethyl compound is reacted with tert-butyl lithium in organic solution, for example in pentane, tetrahydrofuran or ether, or in a mixture of these solvents, N-trimethylsilyl-2-pyrrolidinone is then added and the mixture is left to react, preferably below 0° C., the solution obtained is hydrolyzed, the organic phase is recovered, dried and purified to obtain the required 2-(1-alkoxyethenyl)-1-pyrroline. The hydrolysis is preferably carried out by addition of water or a solution of ammonium chloride. After hydrolysis, a salt, such as sodium chloride, may be added to saturate the solution so that the yield of the process can be improved.

The final purification step may be carried out by any method, such as distillation and/or column chromatography. Accordingly, compounds of the 2-(1-alkoxyethenyl)-1-pyrroline type can be obtained by this process and may be used for the production of encapsulated 2-acetyl-1-pyrroline.

It has also been found that one of the compounds of this type, namely 2-(1-ethoxyethenyl)-1-pyrroline, has certain organoleptic qualities which enable it to be used on its own or in combination as a flavouring agent. These organo-leptic characteristics may be described as grilled, fruity, hazel nuts and reminiscent of those of pyrazine. Thus, 2-(1-ethoxyethenyl)-1-pyrroline may be used on its own as a flavouring agent, for example as a substitute for certain alkyl pyrazines. The quantity to be added to a food product depends primarily on the nature of the product and on the final effect required.

2-(1-Ethoxyethenyl)-1-pyrroline may also be used in the preparation of a flavouring composition, for example a flavouring composition containing up to 0.1% by weight 2-(1-ethoxyethenyl)-1-pyrroline, which has a flavour of corn, bread or potatoes. The composition thus obtained may be added to the end food product in a quantity of 1 to 2 grams per kilo end product.

EXAMPLES

The invention is illustrated in more detail in the following Examples in which parts and percentages are by weight and wherein:

Example 1 describes a process for the production of 2-1-ethoxyethenyl)-1-pyrroline.

Example 2 describes the tests for identifying this compound.

Example 3 illustrates the flavouring properties of this compound.

Examples 4 and 5 illustrate two processes for the production of 2-acetyl-1-pyrroline in aqueous solution.

Examples 6 to 9 illustrate three processes for the production of 2-acetyl-1-pyrroline in encapsulated form and the product obtained.

Example 10 illustrates the stability in storage of the encapsulated 2-acetyl-1-pyrroline.

Examples 11 to 16 illustrate the properties of the encapsulated 2-acetyl-1-pyrroline either on its own or in a taste exhauster composition.

EXAMPLE 1

A solution containing 54.1 g ethylvinyl ether in 300 ml tetrahydrofuran (THF) is prepared.

This solution is cooled to −40° C. and a 1.4N solution of 429 ml tert. butyl lithium in pentane is added dropwise to the solution. The mixture is then stirred continuously for 12 hours at −40° C., after which a solution of 47.1 g of N-trimethylsilyl-2-pyrrolidinone in 300 ml THF is added. The mixture thus obtained is stirred continuously for 7 hours at −40° C., after which 32.1 g ammonium chloride dissolved in 300 ml water are added. The mixture is then left to return to approximately 0° C. and is then saturated by addition of 60 g sodium chloride. The solution is then left standing so that the aqueous phase and organic phase can separate. The organic phase is recovered and the aqueous phase is extracted three times with 50 ml ether.

The various organic fractions obtained are mixed, washed three times with 50 ml water saturated with NaCl and then dried over sodium sulfate and the solvents are evaporated under reduced pressure. 37.8 g crude extract are obtained in the form of a yellow liquid. A chromatography column 4 cm in diameter and 80 cm in height containing 500 g of a silica gel is prepared. A solution containing 20 parts dichloromethane to 1 part ethyl acetate is used as eluent. The crude extract diluted with the eluent is introduced into the column and is then eluted at a rate of 2 ml per minute. A 99.9% pure compound in the form of a colourless liquid is obtained in a yield of 17.1 g.

EXAMPLE 2

1. Mass spectrum

The mass spectrum of the compound obtained in accordance with Example 1 gives the following results:

| m/z | Relative intensity (100 = base peak) | Identification |
| --- | --- | --- |
| 139 | 8 | [M] + Molecular peak |
| 124 | 21 | [M-CH$_3$] + |
| 110 | 5 | [M-C$_2$H$_5$] + |
| 95 | 100 | [M-CH$_3$CHO] + |
| 94 | 66 | [M-OC$_2$H$_5$] + |
| 83 | 6 | — |
| 82 | 10 | — |
| 67 | 18 | — |
| 41 | 30 | — |

2. Elemental analysis

Elemental analysis of the compound obtained in accordance with example 1 by combustion gave the following results:

| | | % |
| --- | --- | --- |
| C | Observed | 68.70 |
|   | Calculated | 69.03 |
| H | Observed | 9.26 |
|   | Calculated | 9.41 |
| N | Observed | 9.74 |
|   | Calculated | 10.06 |

The calculated results are for a compound having the approximate formula $C_8H_{13}NO$ and a molecular weight M of 139.198 g.

3. Infrared spectrum

The infrared spectrum of the compound obtained in accordance with Example 1 in the form of a film gives the following results:

| Frequency of the characteristic bands (cm$^{-1}$) | % Transmission |
| --- | --- |
| 2977 | 23.8 |
| 2932 | 28.9 |
| 2862 | 34.5 |
| 1738 | 45.8 |
| 1612 | 26.9 |
| 1591 | 20.5 |
| 1370 | 29.7 |
| 1322 | 19.7 |

| Frequency of the characteristic bands (cm$^{-1}$) | % Transmission |
| --- | --- |
| 1271 | 25.1 |
| 1129 | 20.6 |
| 1068 | 25.6 |
| 979 | 34.7 |
| 819 | 30.2 |

4. NMR spectrum

The nuclear magnetic resonance spectrum of the proton of the compound in trichlorodeuteromethane (CDCl$_3$) at 20° C. shows the following characteristic signals:

| Signal (ppm) | Multiplicity of the signal | Coupling constant (Hz) | Identification |
| --- | --- | --- | --- |
| 4.73 | Doublet | 2.6 | H Olefinic |
| 4.52 | Doublet | 2.6 | H Olefinic |
| 4.02 | Triplet of a triplet | 2.0 and 7.4 | 2H-5 |
| 3.87 | Quadruplet | 7 | 2H Ethyl |
| 2.73 | Multiplet |  | 2H-3 |
| 1.93 | Multiplet |  | 2H-4 |
| 1.42 | Triplet | 7 | 3H Ethyl |

Accordingly, the compound can be identified by these four tests as being 2-(1ethoxyethenyl)-1-pyrroline corresponding to the following formula:

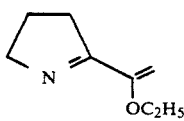

EXAMPLE 3 a) Detection of the perception threshold by direct olfaction

Several aqueous solutions containing 2-(1-ethoxyethenyl)-1-pyrroline in various concentrations are prepared.

50 ml of each solution accommodated in a 250 ml Erlenmeyer flask provided with a cover are presented to six tasters skilled in the analysis of aromas.

The test is carried out as follows:

Three flasks are presented to each taster: one flask containing the aromatic solution and two flasks containing water. The taster has to sniff the head space and designate the flask containing the aromatic solution. The test is repeated twice for concentrations of 100, 100, 10, 5 and 1 ppm.

The following results are obtained:

| Concentration (ppm) | 1000 | 100 | 10 | 5 | 1 |
| --- | --- | --- | --- | --- | --- |
| Positive olfaction (%) | 100 | 100 | 100 | 50 | 17 |

Accordingly, the perception threshold by direct olfaction is of the order of 5 ppm.

b) Detection of the perception threshold by GC sniffing

The minimum quantity of 2-(1-ethoxyethenyl)-1-pyrroline detectable by olfaction is determined by GC sniffing (a combination of gas chromatography and olfactometry). To this end, solutions of the compound in various concentrations are analyzed by gas phase chromatography.

After orientation tests, solutions of 2-(1-ethoxyethenyl)1-pyrroline in dichloromethane are prepared in concentrations of 100, 500 and 1000 ppm.

The analyses are carried out under the following conditions:

| | |
| --- | --- |
| • Chromatograph | HP 5890 A (Hewlett Packard) |
| • Capillary column | DB wax (J and W Scientific), length 30 m, i.d. 0.25 mm |
| • Detection | FID, 250° C. + sniffing port, 150° C. effluent splitting: 1/1 |
| • Injection | 200° C., split (27.7 ml/min.) |
| • Gas vector | helium, 17.5 psi |
| • Furnace temperature: | 100° C. − 4° C./min. − 180° C. |
| • Quantity injected: | 1 microliter of a 1000 ppm solution, i.e., 1 microgram of the compound. |
| • Gas flows: | split vent = 27.7 ml/min. column effluent = 0.6 ml/min. (sniffing port) |
| • Quantity of 2-(1-ethoxyethenyl)-1-pyrroline arriving at the sniffing port = 21.7 ng | |
| • Estimation of the air volume entraining the 2-(1-(ethoxyethenyl)-1-pyrroline | |
| • Duration of olfactory peak = 5 seconds | |
| • Humidified air flow rate (make up) = 0.83 ml/sec. | |
| • Air volume estimated at 4.2 ml air. | |

The perception threshold of 2-(1-ethoxyethenyl)-1-pyrroline is 21.7 ng in 4.2 ml air, i.e., 5.20 ng/ml air.

EXAMPLE 4

2-(1-Ethoxyethenyl)-1-pyrroline is hydrolyzed by addition of 5 ml 10.5N hydrochloric acid to 67.74 mg 2-(1-ethoxyethenyl)-1-pyrroline at 0° C. The mixture is then left standing for 2 hours at ambient temperature (25° C.).

The mixture is then cooled to approximately 5° C. and neutralized by dropwise addition with continuous stirring of 52.5 ml 1N sodium hydroxide. An aqueous solution containing 97% 2-acetyl-1-pyrroline, i.e., 52.40 mg, and 3% 2-acetyl-2-pyrroline, i.e., 1.62 mg (composition determined by gas phase chromatography and mass spectrometry) is obtained.

EXAMPLE 5

2-(1-Ethoxyethenyl)-1-pyrroline is hydrolyzed by addition of 5 mn 1N hydrochloric acid to 69.81 mg 2-(1-ethoxyethenyl)-1-pyrroline at 0° C. The mixture is then left standing for 7 days at ambient temperature (25° C.) so that hydrolysis is complete.

The mixture is then cooled to approximately -5° C. and the hydrolyzed mixture is diluted with 40 ml water and then neutralized by dropwise addition with continuous stirring of 5 ml 1N sodium hydroxide.

An aqueous solution containing 54 mg 2-acetyl-1-pyrroline (97%) and 1.67 mg 2-acetyl-2-pyrroline (3%) is obtained.

EXAMPLE 6

70 ml 1N HCl are added to 1.00132 g 2-(1-ethoxyethenyl)-1-pyrroline (i.e., 7.20 mmol) at 0° C. and the mixture is left standing for 7 days at ambient temperature.

A first sample A of 17.5 ml of this reaction mixture is diluted in 175 ml water and cooled to 0° C. 17.5 ml 1N NaOH and an aqueous solution containing 17.6 g maltodextrin, 2.4 g gum arabic and 430 ml water are then added dropwise. The solution thus obtained is freeze-dried in a standard freeze dryer. A white powder containing 2-acetyl-1-pyrroline in a concentration of 1.0%, based on the maltodextrin/gum arabic mixture, and in a concentration of 0.94%, based on the powder, is obtained.

EXAMPLE 7

A sample B of 13.125 ml of the reaction mixture obtained in Example 6 is diluted in 130 ml water and cooled to 0° C. 13.125 ml 1N NaOH and then an aqueous solution containing 15 g β-cyclodextrin in 400 ml water are then added dropwise. The solution thus obtained is freeze-dried as in Example 6. A white powder containing 2-acetyl-1-pyrroline in a concentration of 1.0%, based on the β-cyclodextrin, and in a concentration of 0.94%, based on the powder, is thus obtained.

EXAMPLE 8

A sample C of 13.125 ml of the reaction mixture obtained in Example 6 is diluted in 100 ml water and then cooled to 0° C. 15.0 g β-cyclodextrin in powder form and 13.125 ml 1N NaOH are then added. After stirring for 30 minutes at 0° C., the solution is freeze-dried as in Example 6. In this case, freeze-drying is easier to carry out because the volume of water is much smaller by comparison with Examples 6 and 7.

A white powder containing 2-acetyl-1-pyrroline in a concentration of 1.0%, based on the β-cyclodextrin, and 0.94%, based on the powder, is obtained.

EXAMPLE 9

A sample D of 13.125 ml of the reaction mixture obtained in Example 6 is diluted in 130 ml water and cooled to 0° C. 13.125 ml 1N NaOH and an aqueous solution containing 1.5 g β-cyclodextrin in 40 ml water are then added dropwise. The solution thus obtained is freeze-dried as in Example 6. A white powder containing 2-acetyl-1-pyrroline in a concentration of 10.0%, based on the β-cyclodextrin, is obtained.

EXAMPLE 10

The stability of the encapsulated 2-acetyl-1-pyrroline prepared in accordance with Examples 6 to 9 is studied over a period of 110 days at various storage temperatures. To this end, samples of 100 mg freeze-dried powder are taken after storage and dissolved in 1 ml water at 0° C. 1 ml ethyl acetate containing 1 mg trimethyl-2,4,6-pyridine is added and the mixture is stirred for 30 seconds. The mixture is then centrifuged for 15 minutes at −5° C. and the organic phase is recovered and analyzed by gas phase chromatography.

The percentage of 2-acetyl-1-pyrroline being decomposed after 110 days storage is then determined. The following results are obtained:

Support and concentration of 2-acetyl-1-pyrroline

| Storage temperature | Maltodextrin 1% | β-Cyclodextrin 1% | β-Cyclodextrin 10% |
| --- | --- | --- | --- |
| 20° C. | Complete decomposition after 50 d | 99% | 91% After 13 days |
| 4° C. | 33% | 10% | 13% After 23 days |
| −20° C. | 13% | 0% | — |

It can be seen that 2-acetyl-1-pyrroline encapsulated in a concentration of 1% on β-cyclodextrin remains stable for at least 110 days when stored at a low temperature. This is also the case, although to a lesser extent, if the 2-acetyl-1-pyrroline is encapsulated in a concentration of 1% on maltodextrin/gum arabic. By contrast, the stability of the 2-acetyl-1-pyrroline decreases when its concentration on the support (in the present case β-cyclodextrin) increases. By comparison, 95% pure 2-acetyl-1-pyrroline prepared in accordance with the prior art degrades rapidly in storage at −20° C. (Buttery, et al., Journal of Agric. Food Chem. (1983), 31, 823–826).

EXAMPLE 11

1 ppm 2-acetyl-1-pyrroline encapsulated in a concentration of 1% on β-cyclodextrin is added to a corn soup just before consumption. The soup thus prepared and a control soup containing no 2-acetyl-1-pyrroline are presented to a group of six trained tasters. The 2-acetyl-1-pyrroline contributes towards a rounder, more cooked and more pleasant perception of the food. The "cooked cereal", "popcorn" and "very slightly grilled" notes are strengthened and developed together with a very fine "buttery-fresh" note.

EXAMPLE 12

1 ppm 2-acetyl-1-pyrroline encapsulated in a concentration of 1% on β-cyclodextrin is added to a chicken soup just before its consumption. The soup thus prepared and a control soup containing no 2-acetyl-1-pyrroline are presented to a group of six trained tasters. The 2-acetyl-1-pyrroline contributes towards reducing the "chicken fat" note and strengthens the "chicken meat" and "slightly grilled" notes. The whole is more cooked and more complete and the slight "grilled meat" aftertaste is prolonged.

EXAMPLE 13

1 ppm 2-acetyl-1-pyrroline encapsulated in a concentration of 1% on β-cyclodextrin is added to a beef soup just before consumption. The soup thus prepared and a control soup containing no 2-acetyl-1-pyrroline is presented to a group of six trained tasters. The 2-acetyl-1-pyrroline contributes towards strengthening the "slightly grilled meat" note. The impression in the mouth is more round and the beef aftertaste is prolonged.

EXAMPLE 14

A taste exhauster composition of the "breadcrust" type is prepared by adding the following compounds 1 litre ethanol: 50 g 2-acetyl pyrazine, 10 g 2-acetyl thiazole, 30 g diacetyl, 5 g 2-ethyl-3-methyl pyrazine. 0.1 g of this composition is added to 1 litre water previously salted with 3 g NaCl per litre. The aqueous mixture is divided into two batches. 0.5 ppm 2-acetyl-1-pyrroline encapsulated in a concentration of 1% on β-cyclodextrin is added to the first batch. The second batch serves as control. A panel of ten people compares the two batches. The first batch appears better than the second with a strengthened "cereal", "breadcrust" note and a rounded "grilled" note. The whole remains longer in the mouth. When added to a pizza dough, the present composition strengthens the "breadcrust" note, above all on olfaction.

EXAMPLE 15

A taste exhauster composition of the "corn" type is prepared by adding the following compounds to 1 litre ethanol: 5 g 2-acetyl pyrazine, 5 g 2-acetyl thiazole, 0.5 g diacetyl, 20 g dimethyl sulfide. 0.1 g of this composition is added to 1 litre water salted beforehand with 3 g NaCl per litre the aqueous mixture is divided into two batches. 0.5 ppm 2-acetyl-1-pyrroline encapsulated in a concentration of 1% on β-cyclodextrin is added to the first batch. The second batch serves as control. A panel of 10 people compares the two batches. The first batch has a more marked, more complete and more powerful "sweet corn" and "popcorn" note. Persistence in the mouth is more pronounced.

EXAMPLE 16

A taste exhauster composition of the "potato" type is prepared by adding the following compounds to 1 litre ethanol: 5 g 2-acetyl thiazole, 5 g trimethyl pyrazine, 0.5 g diacetyl, 2 g 2-ethyl-3-methoxypyrazine, 50 g methylthio-3-propanal. 0.1 g of this composition is added to 1 litre water salted beforehand with 3 g NaCl per litre. The aqueous mixture is divided into two batches. 0.5 ppm 2-acetyl-1-pyrroline encapsulated in a concentration of 1% on β-cyclodextrin is added to the first batch. The second batch serves as control. A panel of 10 people compares the two batches. The first batch appears better than the second and has a more complete and strengthened note of the "cooked potato flesh" type.

We claim:
1. A 2-(1-alkoxyethenyl)-1-pyrroline compound.
2. 2-(1-ethoxyethenyl)-1-pyrroline.

* * * * *